Figure 1:
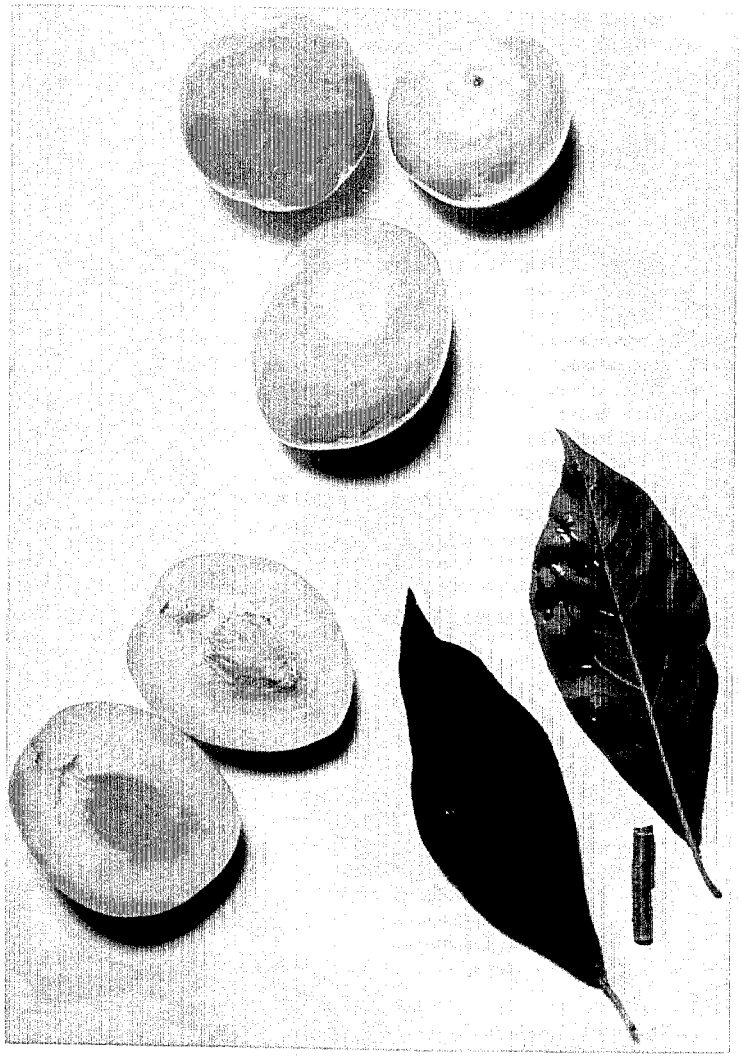

United States Patent [19]

Hengst

[11] Plant 4,977

[45] Jan. 25, 1983

[54] PLUM TREE

[75] Inventor: William E. Hengst, Exeter, Calif.

[73] Assignee: Alan D. Ewen, Sacramento, Calif.

[21] Appl. No.: 314,924

[22] Filed: Oct. 26, 1981

[51] Int. Cl.[3] ..... A01H 5/03

[52] U.S. Cl. ..... Plt./38

[58] Field of Search ..... Plt./38

*Primary Examiner*—Robert E. Bagwill

*Attorney, Agent, or Firm*—Townsend and Townsend

[57] ABSTRACT

A new and distinct Japanese plum tree which is an open pollinated seedling of Mariposa and which is characterized by its yellow skin color. Compared with Mariposa this new variety matures in the Exeter District 3 weeks later. The fruit has an elongate rather than a round shape. The fruit holds well in storage and at room temperature, as well or better than Mariposa, and is suitable for the fresh and dried fruit markets.

1 Drawing Figure

This invention relates to a new and distinct variety of plum tree of the Salicina species, commonly called Japanese plum, the fruit of which is suitable for the fresh and dried fruit markets.

The new variety is an open pollinated seedling of Mariposa and was discovered by me growing among plantings of Mariposa plum trees on my farm in Exeter, Calif. in 1976.

The new variety, which I call the Bill Hengst Golden Nectar Plum, was reproduced by grafting at 18656 Avenue 296, Exeter, Calif.

The FIGURE illustrates the external views of the fruit of the new variety, a longitudinal sectional view of the fruit of the new variety showing the pit embedded in one half, two views of a leaf of the new variety and a side view of a section of branch of the new variety.

PLANT CHARACTERISTICS

The color references listed below refer to the book, *Dictionary of Color*, A. Maerz and M. Rea Paul, McGraw-Hill Book Company, Inc., New York, N.Y., 2nd Edition, 1950.

The most significant feature of this new variety is that the fruit has a yellowish green color (Wax Y—page 45, plate 11, L-4), similar to Kelsey, but is more elongated in shape and matures earlier than Kelsey.

Tree: medium size, figure medium spreading, productive and regular bearing. The trunk has a medium diameter in relation to length and medium rough surface characteristics with fine vertical cracks in the bark. The branches are medium in size and have a medium rough surface character and are multicolored with a base color and lighter color where bark is cracked open; the base color of the branches is Chutney (page 37, plate 7, J-12) and the top color of the branches is Sepia (page 39, plate 8, A-10); the lenticels are numerous and are about 0.5–1×2–4 mm. The leaves are large having a length of 120–130 mm and a width of 37–42 mm; the shape is eliptical with acute apice; the color of the upper surface is Cedar Green (page 69, plate 23, J-6) while the lower surface is Polo Green (page 69, plate 23, J-10); the marginal form is double serrate while the glandular characteristics are 2, opposite reniform; the petiole is about 18–25 mm long and about 2 mm thick; the stem glands number 0–1, have an irregular arrangement, are reddish brown in color and are of the reniform type.

Flower buds: small, having a short and plump shape and a glabrous surface.

Flowers: first bloom in the Exeter District of California is about February 12 with full bloom about February 25. The flowers are small and white.

Fruit: reach maturity July 25–30 in the Exeter District of California which is about three weeks later than the Mariposa variety. The fruit is uniformly large in size having a diameter of 60 mm, a transverse dimension in suture plane of 63 mm and a transverse dimension at right angles to suture plane of 78 mm. The fruit has a uniform form, is oblong and beaked and has a distinct and shallow suture 105–110 mm long. The ventral surface is rounded slightly and smooth while the stem cavity is obtuse with a width of 15–20 mm and a depth of 5 mm. The base is truncate and the apex is prolonged and beaked. The stem is medium with a length of 15 mm and a width of 2 mm. The skin is thin, has a tender texture, no pubesence and has no tendency to crack. The skin color is Wax Y (page 45, plate 11, L-4). The flesh color is Peach Blow+ (page 43, plate 10, E-5). The surface of the pit cavity is rough with some shallow grooves and the color of the pit well is Dorado Honey Beige+ (page 45, plate 11, H-6). The juice is moderate having a subacid flavor and a very slight aroma. The texture is firm and the fibers are few, fine and tender. The flesh ripens evenly and has good eating quality both fresh and dried.

Stone: free, length 30 mm, breadth 20 mm and thickness 10 mm. The stone is oval, flattened at base and is abruptly pointed at apex. The surface is slightly ridged throughout with jagged ridges and has elongated pits toward the base. The ventral suture is narrow and thin while the dorsal suture is narrow with shallow grooves near the base. The stone has two irregularly patterned colors: Golen Wheat (page 45, plate 11, F-7) and Olive Wood Collie (page 53, plate 15, E-10).

Kernel: ovate in form, 10–11 mm×16–17 mm in size. Amygdalin is moderate and the color is Formosa (page 47, plate 12, H-8).

Keeping quality of fruit: good; holds well at storage and at room temperature, as well as or better than Mariposa.

Use of fruit: fresh market and dried.

I claim:

1. A new and distinct variety of plum tree as described, illustrated and identified by the characteristics enumerated above.

* * * * *